(12) United States Patent
Pellecchia et al.

(10) Patent No.: US 11,732,007 B2
(45) Date of Patent: Aug. 22, 2023

(54) THERAPEUTIC COMPOUNDS AND METHODS

(71) Applicant: The Regents of the University of California, Oakland, CA (US)

(72) Inventors: Maurizio Pellecchia, San Diego, CA (US); Carlo Baggio, Moreno Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/486,602

(22) Filed: Sep. 27, 2021

(65) Prior Publication Data

US 2022/0098238 A1 Mar. 31, 2022

Related U.S. Application Data

(60) Provisional application No. 63/084,387, filed on Sep. 28, 2020.

(51) Int. Cl.
*C07K 5/117* (2006.01)
*A61P 37/06* (2006.01)

(52) U.S. Cl.
CPC ............ *C07K 5/1024* (2013.01); *A61P 37/06* (2018.01)

(58) Field of Classification Search
None
See application file for complete search history.

(56) References Cited

U.S. PATENT DOCUMENTS

| | | |
|---|---|---|
| 2004/0180823 A1 | 9/2004 | Pasquale et al. |
| 2010/0166657 A1 | 7/2010 | Kinch et al. |
| 2010/0197688 A1 | 8/2010 | Nantermet et al. |
| 2015/0274777 A1 | 10/2015 | Lynch et al. |
| 2018/0127464 A1 | 5/2018 | Pellecchia et al. |

FOREIGN PATENT DOCUMENTS

WO 2016019280 A1 2/2016

OTHER PUBLICATIONS

Amara et al. ('Synthetic fluorogenic peptides reveal dynamic substrate specificity of depalmitoylases' Cell Chemical Biology v26 Jan. 17, 2019, pp. 35-47 and e1-e7 for a total of 20 pages) (Year: 2019).*
Baggio et al. ('HTS by NMR for the identification of potent and selective inhibitors of metalloenzymes' ACS Medicinal Chemistry Letters v9 2018 pp. 137-142) (Year: 2018).*
Baggio et al. supplement (Supplement information for ('HTS by NMR for the identification of potent and selective inhibitors of metalloenzymes' ACS Medicinal Chemistry Letters v9 2018, 8 pages) (Year: 2018).*
Baggio, C , et al., "Therapeutic Targeting of MMP-12 for the Treatment of Chronic Obstructive Pulmonary Disease", J Med Chem 63 (21), 12911-12920 (2020).
Solun, B , et al., "Inhibition of metalloproteinases in therapy for severe lung injury due to COVID-19", Med Drug Discov 7, 100052, 5 pages (2020).

* cited by examiner

*Primary Examiner* — Ronald T Niebauer
(74) *Attorney, Agent, or Firm* — Viksnins Harris Padys Malen LLP (57) ABSTRACT

Provided is a compound of formula (I):

$$R_1\text{-NH-CH}(R^2)\text{-C(O)-NH-CH}(R^3)\text{-C(O)-NH-CH}(R^4)\text{-C(O)-R^5}$$

(I)

or a salt thereof, wherein $R^1$-$R^5$ have any of the values described in the specification, as well as compositions comprising a compound of formula (I) or a pharmaceutically acceptable salt thereof and therapeutic methods comprising the administration of a compound of formula (I) or a pharmaceutically acceptable salt thereof. The compounds are useful as matrix metalloprotease MMP-12 inhibitors.

2 Claims, 4 Drawing Sheets

THERAPEUTIC COMPOUNDS AND METHODS

CROSS-REFERENCE TO RELATED APPLICATION(S)

This application claims priority to U.S. Provisional Application No. 63/084,387, filed on Sep. 28, 2020. The entire content of the application referenced above is hereby incorporated by reference herein.

BACKGROUND

Chronic obstructive pulmonary disease (COPD) is a lung disease characterized by a progressive and irreversible airflow limitation, and currently ranks among the top leading causes of death worldwide. COPD is often associated with an excessive inflammatory response of the lungs to air pollutants, or cigarette smoking. Given the persisting prevalence of cigarette smoking, and the increasing environmental factors and pollutants, the incidence of COPD is expected to continue grow. Moreover COPD has been linked to other sever co-morbidities including cardiovascular disease and lung cancer. Currently, only a few disease-modifying targeted therapeutics are available for this indication. Recent studies with a series of genetically engineered mice revealed, however, that the matrix metalloprotease MMP-12 can play a pivotal role in airway inflammation and remodeling. Preclinical studies in COPD/emphysema provide experimental support that approaches aimed at blocking MMP-12 could be translated into useful agents for therapeutic intervention. For example, pathological evidence indicates that MMP-12-deficient mice are protected against the development of emphysema induced by cigarette smoke and pollutants.

There is currently a need for effective treatments for MMP-12 mediated conditions, such as, for example, COPD. In particular, there is a need for effective and selective MMP-12 inhibitors.

SUMMARY

Effective and selective MMP-12 inhibitors have been identified. These MMP-12 inhibitors are useful for the treatment of diseases and conditions mediated by MMP-12, including COPD.

Accordingly, provided in one embodiment is a compound of formula (I):

(I)

or a salt thereof, wherein:

$R^1$ is $(C_2-C_6)$alkanoyl that is substituted with morpholino or piperazino, which morpholino and piperazino is optionally substituted with one or more groups independently selected from the group consisting of $C_1-C_6$)alkyl, $(C_1-C_6)$alkoxy, $(C_1-C_6)$alkoxycarbonyl, $(C_1-C_6)$alkanoyloxy, halo, halo$(C_1-C_6)$alkyl, hydroxy, and halo$(C_1-C_6)$alkoxy;

$R^2$ is $(C_1-C_6)$alkyl that is substituted with a 6-10 membered aryl or a 6-10 membered heteroaryl or $R^2$ is $(C_1-C_6)$alkyl that is substituted with a $(C_1-C_6)$alkoxy that is substituted with 6-10 membered aryl or a 6-10 membered heteroaryl, wherein any 6-10 membered aryl or a 6-10 membered heteroaryl of $R^2$ is optionally substituted with one or more groups independently selected from the group consisting of $(C_1-C_6)$alkyl, $(C_1-C_6)$alkoxy, $(C_1-C_6)$alkoxycarbonyl, $(C_1-C_6)$alkanoyloxy, halo, halo$(C_1-C_6)$alkyl, hydroxy, and halo$(C_1-C_6)$alkoxy;

$R^3$ is $(C_1-C_6)$alkyl that is substituted with a 6-10 membered aryl that is optionally substituted with one or more groups independently selected from the group consisting of $(C_1-C_6)$alkyl, $(C_1-C_6)$alkoxy, $(C_1-C_6)$alkoxycarbonyl, $(C_1-C_6)$alkanoyloxy, halo, halo$(C_1-C_6)$alkyl, hydroxy, and halo$(C_1-C_6)$alkoxy;

$R^4$ is benzyl that is optionally substituted with one or more groups independently selected from the group consisting of $(C_1-C_6)$alkyl, $(C_1-C_6)$alkoxy, $(C_1-C_6)$alkoxycarbonyl, $(C_1-C_6)$alkanoyloxy, halo, halo$(C_1-C_6)$alkyl, hydroxy, and halo$(C_1-C_6)$alkoxy;

$R^5$ is —N($R^c$)—OH; and $R^c$ is H or $(C_1-C_6)$alkyl.

Provided in another embodiment is a pharmaceutical composition comprising, a compound of formula (I) or a pharmaceutically acceptable salt thereof and a pharmaceutically acceptable excipient.

Provided in another embodiment is a method for inhibiting the activity of a matrix metalloprotease comprising, contacting the matrix metalloprotease with a compound of formula (I) or a salt thereof.

Provided in another embodiment is a method for treating or preventing a disease or condition mediated by MMP-12 in an animal (e.g., a mammal such as a human) comprising administering a compound of formula (I) or a pharmaceutically acceptable salt thereof to the animal.

Provided in another embodiment is a compound of formula (I) or a pharmaceutically acceptable salt thereof for use in medical therapy.

Provided in another embodiment is a compound of formula (I) or a pharmaceutically acceptable salt thereof for the prophylactic or therapeutic treatment of a disease or condition mediated by MMP-12.

Provided in another embodiment is the use of a compound of formula (I) or a pharmaceutically acceptable salt thereof to prepare a medicament for treating a disease or condition mediated by MMP-12 in an animal (e.g. a mammal such as a human).

Provided in another embodiment are processes and intermediates disclosed herein that are useful for preparing a compound of formula (I) or a salt thereof.

DETAILED DESCRIPTION

The following definitions are used, unless otherwise described: halo or halogen is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkoxy" refers to an alkyl groups attached to the remainder of the molecule via an oxygen atom ("oxy").

The term "aryl" as used herein refers to a single all carbon aromatic ring or a multiple condensed all carbon ring system wherein at least one of the rings is aromatic. For example, in certain embodiments, an aryl group has 6 to 10 carbon atoms. Aryl includes a phenyl radical.

Aryl also includes multiple condensed carbon ring systems (e.g., ring systems comprising 2 rings) having about 9 to 10 carbon atoms in which at least one ring is aromatic and wherein the other rings may be aromatic or not aromatic (i.e., cycloalkyl). The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, and 1, 2, 3, 4-tetrahydronaphthyl.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms.

Exemplary heterocycles include but are not limited to azetidinyl, tetrahydrofuranyl and piperidinyl. The term "heterocycle" also includes multiple condensed ring systems (e.g., ring systems comprising 2 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein a wavy line "⁓" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient In one embodiment, the patient is a human patient.

The term "disease or condition mediated by MMP-12" includes any disease or condition where the activity of MMP-12 is implicated and inhibition of the activity of MMP-12 provides a therapeutic benefit. For example, see Vandenbroucke, R. E., et al., *Eur. Respir.* 2011, 38, 1200-1214; and Chelluboina, B., et al., *Mol. Neurobiol,* 2018, 55, 1405-1409. Such diseases and conditions include inflammatory conditions infecting the lungs including asthma and COPD, as well as pulmonary fibrosis, lung cancer, neurological diseases, and psoriasis. Moreover, MMP12 inhibition could ameliorate or prevent severe acute lung injury (ALI) and ARDS (acute respiratory distress syndrome) due to SARS-CoV2 and related viral lung diseases such as COVID-19 (for example, Solun et al., Medicine in Drug Discovery, 2020, 7, 100052.

The compounds disclosed herein can also exist as tautomeric isomers in certain cases. Although only one delocalized resonance structure may be depicted, all such forms are contemplated.

The compounds of formula (I) include compounds enriched at any or all atoms above naturally occurring isotopic ratios with one or more isotopes such as, but not limited to, deuterium ($^2$H or D). As a non-limiting example, a —$CH_3$ group may be substituted with —$CD_3$.

The pharmaceutical compositions can comprise one or more excipients. When used in combination with the pharmaceutical compositions the term "excipients" refers generally to an additional ingredient that is combined with the compound of formula (I) or the pharmaceutically acceptable salt thereof to provide a corresponding composition. For example, when used in combination with the pharmaceutical compositions the term "excipients" includes, but is not limited to: carriers, binders, disintegrating agents, lubricants, sweetening agents, flavoring agents, coatings, preservatives, and dyes.

Stereochemical definitions and conventions used herein generally follow S. R Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds can contain asymmetric or chiral centers, and therefore exist in different stereoisomeric forms. It is intended that all stereoisomeric forms of the compounds, including but not limited to, diastereomers, enantiomers and atropisomers, as well as mixtures thereof such as racemic mixtures, are included as compounds of formula (I). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds having a chiral center may exist in and be isolated in optically active and racemic forms. Some compounds may exhibit polymorphism. It is to be understood that formula (I) encompasses any racemic, optically-active, polymorphic, or stereoisomeric form, or mixtures thereof, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is ($C_2$-$C_4$)alkanoyl that is substituted with morpholino that is optionally substituted with one or more groups independently selected from the group consisting of $C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^1$ is ($C_2$-$C_4$)alkanoyl that is substituted with morpholino.

A specific value for $R^1$ is ($C_2$-$C_4$)alkanoyl that is substituted with piperazino that is optionally substituted with one or more groups independently selected from the group consisting of $C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^1$ is ($C_2$-$C_4$)alkanoyl that is substituted with piperazino that is optionally substituted with one or more groups independently selected from the group consisting of $C_1$-$C_6$)alkyl.

A specific value for $R^1$ is ($C_2$)alkanoyl that is substituted with morpholino that is optionally substituted with one or more groups independently selected from the group consisting of $C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^1$ is ($C_2$)alkanoyl that is substituted with morpholino.

A specific value for $R^1$ is ($C_2$)alkanoyl that is substituted with piperazino that is optionally substituted with one or more groups independently selected from the group consisting of $C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^1$ is ($C_2$)alkanoyl that is substituted with piperazino that is optionally substituted with one or more groups independently selected from the group consisting of $C_1$-$C_6$)alkyl.

A specific value for $R^2$ is ($C_1$-$C_6$)alkyl that is substituted with a 6-10 membered aryl or a 6-10 membered heteroaryl, wherein any 6-10 membered aryl or a 6-10 membered heteroaryl of $R^2$ is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^2$ is ($C_1$-$C_6$)alkyl that is substituted with a ($C_1$-$C_6$)alkoxy that is substituted with 6-10 membered aryl or a 6-10 membered heteroaryl, wherein any 6-10 membered aryl or a 6-10 membered heteroaryl of $R^2$ is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^2$ is ($C_1$-$C_6$)alkyl that is substituted with phenyl, naphthyl, or indolyl, which phenyl, naphthyl, and indolyl is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^2$ is ($C_1$-$C_6$)alkyl that is substituted with a ($C_1$-$C_6$)alkoxy that is substituted with phenyl, naphthyl, and indolyl is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^2$ is benzyloxymethyl, 3-phenylpropyl, 3-indolylmethyl2-naphthylmethyl, or 3-(4-methoyphenyl)propyl.

A specific value for $R^3$ is ($C_1$-$C_3$)alkyl that is substituted with a 6-10 membered aryl that is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^3$ is ($C_1$-$C_6$)alkyl that is substituted with phenyl that is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy; A specific value for $R^3$ is ($C_1$-$C_3$)alkyl that is substituted with phenyl that is optionally substituted with one or more groups independently selected from the group consisting of ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^3$ is phenethyl, 3-phenylpropyl, 4-trifluoromethylphenethyl, or 4-methoxyphenethyl.

A specific value for $R^4$ is benzyl that is optionally substituted with one or more groups independently selected from the group consisting of hydroxy, fluoro, chloro, trifluoromethyl, m ethoxy carbonyl, and methyl.

A specific value for $R^4$ is:

wherein, $R^d$ is H or F; and $R^e$ and $R^f$ are each independently selected from the group consisting of H, ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^4$ is:

wherein, $R^e$ is H, Cl, or methyl; and $R^d$ and $R^f$ are each independently selected from the group consisting of H, ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^4$ is:

wherein, $R^f$ is H, Cl, or methyl; and $R^d$ and $R^e$ are each independently selected from the group consisting of H, ($C_1$-$C_6$)alkyl, ($C_1$-$C_6$)alkoxy, ($C_1$-$C_6$)alkoxycarbonyl, ($C_1$-$C_6$)alkanoyloxy, halo, halo($C_1$-$C_6$)alkyl, hydroxy, and halo($C_1$-$C_6$)alkoxy.

A specific value for $R^5$ is —N(H)—OH.

A specific compound of formula (I) is a compound of formula (Ia):

A specific compound of formula (I) is a compound of formula (I) is a compound of formula (Ib):

A specific compound of formula (I) is a compound of formula (I) is a compound of formula (Ic):

A specific compound of formula (I) is a compound of formula (I) is a compound of formula (Id):

A specific compound is a compound selected from the group consisting of:

or a salt thereof.

In cases where compounds are sufficiently basic or acidic, a salt of a compound of formula (I) can be useful as an intermediate for isolating or purifying a compound of formula (I). Additionally, administration of a compound of formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human patient in a variety of forms adapted to the chosen route of administration. The compounds can be administered orally, via IV injection, or aerosolized using formulations that may be obtained by conventional procedures well known in the pharmaceutical art.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds can also be administered in combination with other therapeutic agents, for example, other agents that are useful for the treatment of COPD. Examples of such agents include but are not limited to corticosteroids, short- and long-acting bronchodilators, methylxanthines, roflumilast, mucoactive drugs, etc.

Accordingly, also provided is a composition comprising a compound of formula (I), or a pharmaceutically acceptable salt thereof, at least one other therapeutic agent, and a pharmaceutically acceptable diluent or carrier. Also provided is a kit comprising a compound of formula (I), or a pharmaceutically acceptable salt thereof, at least one other therapeutic agent, packaging material, and instructions for administering the compound of formula (I) or the pharmaceutically acceptable salt thereof and the other therapeutic agent or agents to an animal to treat COPD.

The following Examples are non-limiting.

EXAMPLES

General Chemistry.

All common solvent and reagents were obtained by commercial sources. NMR spectra were recorded on Bruker Avance III 700 MHz and these were used both for quality control and to verify the concentration of the stock solutions used for dose response measurements and in vivo studies. An Agilent LC-TOF instrument was used to obtain high-resolution mass spectral data. Purification of all agents was obtained using RP-HPLC on a JASCO preparative system equipped with a PDA detector. The instrument is also equipped with a fraction collector controlled by a Chrom-NAV system (JASCO). For all agents, a Luna C18 10μ 10×250 mm (Phenomenex) column was used to purify agents to >95% purity. For intermediate reagents that were not commercially available, RP-chromatography purification was performed using a CombiFlash (Teledyne ISCO). GM6001 was obtained from Enzo Life science. MMP408 was obtained from EMD Millipore Corp.

Example 1. Synthesis of Compounds 25 and 26

-continued

26

Compounds 25 and 26 were synthesized using standard solid-phase synthesis protocols, using an fmoc-hydroxylamine-2-chlorotrityl resin that introduces the hydroxamic acid at the C-terminus of the peptides, after cleavage. For each coupling reaction, 3 eq. of Fmoc-AA, 3 eq. of HATU, 3 eq. of OximaPure, and 5 eq. of DIPEA in 1 ml of DMF were used. The coupling reaction was allowed to proceed for 1 hour. Fmoc deprotection was performed by treating the resin-bound peptide with 20% piperidine in DMF twice. Peptides were cleaved from Rink amide resin with a cleavage cocktail containing TFA/TIS/water (94:3:3) for 3 hours. The cleaving solution was filtered from the resin, evaporated under reduced pressure, the peptides were precipitated in $Et_2O$, centrifuged and dried in high vacuum. The crude peptide was purified by preparative RP-HPLC using a Luna C18 column (Phenomenex) and water/acetonitrile gradient (30% to 70%) containing 0.1% TFA. Both compounds displayed purity>95%. High-resolution mass spectral data were acquired on an Agilent LC-TOF instrument. ID 1H NMR spectra were acquired in d6-DMSO at a concentration of 500 μM on a 700 MHz Bruker Avance III spectrometer equipped with a TCI cryoprobe.

Compound 25

| Calculated Mass | Species | Found Mass |
| --- | --- | --- |
| 687.36 | (M + H)+ | 688.37 |
| | (M + Na)+ | 710.35 |
| | 2M+ | 1375.73 |

Compound 26

| Calculated Mass | Species | Found Mass |
| --- | --- | --- |
| 717.37 | (M + H)+ | 718.38 |
| | (M + Na)+ | 740.36 |
| | 2M+ | 1435.75 |

Intermediate Fmoc protected non-natural amino acids were prepared as follows.

a. Fmoc Protection Non-Natural Amino Acids 1 eq. of the unprotected amino acid and $Na_2CO_3$ were dissolved in THF/H2O (1:1) and cooled to 0° C. 1.1 eq. of Fmoc Chloride was dissolved in THF and added dropwise to the mixture. The reaction was stirred for 2 hours at 0° C. The organic solvent was evaporated under reduced pressure and the pH lowered to 0 using concentrated HCl. The aqueous phase was extracted 3 times with AcOEt and the collected organic phase were dried with $Na_2SO_4$, filtered and evaporated. The resulting crude was purified using a CombiFlash Rf (Teledyne ISCO) using cyclohexane/Ethyl Acetate (10% to 100%). Fmoc protection was required for 4-methoxy-D-homophenylalanine for the synthesis of both compounds 25, and 26; and for (S)-2-Amino-5-(4-methoxyphenyl)pentanoic acid for the synthesis of compound 26.

Example 2. Biological Assays

Protein Expression and Purification

The catalytic domain (Gly106-Gly263) of human macrophage metalloelastase (hMMP-12), was expressed by cloning the gene into a pET21 vector (Novagen) using NdeI and BamHI as restriction enzymes and then transfected into *E. coli* strain BL21 Codon Plus cells. Expression of uniformly $^{15}$N-labeled hMMP-12 in M9 minimal media containing 15 mM ([15]$NH_4)_2SO_4$ was induced with 0.5 mM IPTG at 37° C. for 4 hours. Then protein forms inclusion bodies that were isolated and solubilized in a solution of 8 M urea (in 20 mM Tris-HCl, pH 8). The protein was purified in two steps including a first size-exclusion chromatography (Pharmacia HiLoad Superdex 75 16/60) in 6 M urea (in 50 mM sodium acetate). A second cation exchange purification step was carried using a Mono-S column (Pharmacia) and a sodium chloride linear gradient (from 0 to 500 mM). Protein refolding was accomplished by a multiple dialyses into decreasing concentrations of urea (from 4 M up to 2 M; 50 mM Tris-HCl, pH 7.2, 10 mM $CaCl_2$, 0.1 mM $ZnCl_2$, 300 mM NaCl). Further dialysis steps were performed exchanging the protein into the final buffer containing 20 mM Tris-HCl (pH 7.2), 10 mM $CaCl_2$, 0.1 mM $ZnCl_2$, 300 mM NaCl. The final buffer also contained 200 mM of acetohydroxamic acid (AHA), a weak MMP-12 inhibitor, to prevent the self-proteolysis. Recombinant MMP-1 (Cat. #AS-55575-1), MMP-3 (Cat. #72006), MMP-9 (Cat. #AS-55576-1), MMP-13 (Cat. #AS-72257), and MMP-14 (Cat. #AS-72068) were obtained from AnaSpec.

Enzymatic Assays

Enzymatic assays to profile the inhibitory effects of all the compounds on hMMP-12, and against a panel of 5 closely related MMPs (MMP-1, MMP-3, MMP-9, MMP-13, and MMP-14) were performed using the SensoLyte® 520 Fluorimetric Assay Kit (AnaSpec) for each MMPs. Assay kit for MMP-12 Cat. #AS-71157, MMP-1 Cat. #AS-71150, MMP-3 Cat. #AS-71152, MMP-9 Cat. #AS-71155, MMP-13 Cat. #AS-71156, and MMP-14 Cat. #AS-72025. The assay was performed according to their protocols. Briefly, 10 ng of each MMPs were incubated on a black flat-bottom 96-well plate (Cat. #9502867) at RT for 15 minutes in absence or in presence of different concentration of each compound in a total volume of 50 μL. After 15 minutes, 50 μL of each substrate solution were added. The reagents were mixed together by shaking the plate gently for 30 sec. Immediately after the fluorescence was measured using the VICTOR X5 microplate reader (PerkinElmer) every 3 min for 60 min. All the measurement were performed in duplicates. The $IC_{50}$ values were calculated from dose-response curves using GraphPad Prism 7.

Pharmacokinetics Studies

Compound 25 was administered i.p. (30 mg/kg) to 5 Balb-C mice. Retrorbital bleeding was used to collect blood samples at times 30 min, 1 h, 2 h, 4 h, 8 h, and 24 h and the samples analyzed for compound 25 plasma concentration via extraction followed by LC/MS and compared to a standard calibration curve prepared with purified agent. Compound 25 was soluble in 10% DMSO, 40% PEG400, and 10% (2-hydroxypropyl)-Beta-cyclodextrin in PBS. Mice weight varied between 22 g and 26 g, each receiving approximately 200 μL (weight adjusted to administer 30 mg/Kg of compound 25) of formulated agent. The experiments were conducted at the University of California San Diego in vivo pharmacology core facility, according to a UCSD Institutional Animal Care and Use Committee (IACUC) approved protocol.

Murine Model

C57BL/6 mice were purchased from Jackson Laboratories (Bar Harbor, Me.) and maintained in a pathogen-free vivarium at room temperature with 12-hour light/dark cycles. All mice were 6-8 weeks and both male and female mice were used for the experiment. All animal-use and euthanasia protocols were approved by the UC Riverside Institutional Animal Care and Use Committee (IACUC).

In Vivo Porcine Pancreatic Elastase Exposure

C57BL/6 mice were given a single intranasal instillation with 50 μl of saline or 0.9 U porcine pancreas elastase (Sigma-Aldrich, St. Louis, Mo.) diluted in phosphate buffered saline (IX PBS). Two days following the instillation, mice were treated with 200 μl of vehicle control, MMP-408, compound 25, or compound 26 via intraperitoneal injection. Mice were continually given treatment once a day for 7 consecutive days. Twenty-one days following the initial intranasal instillation, mice were sacrificed. Bronchoalveolar lavage fluid (BALF) was collected by making an incision in the trachea and inserting a cannula with syringe (BD Biosciences, CA), then washing with 1 mL of cold PBS three times. BALF was centrifuged at 1200 RPM for 5 minutes, then cell pellets were combined and resuspended in 200 μl of PBS to be used in cell counts and cell differential analysis. The lungs were isolated, slowly filled with 1 mL of 10% formalin then hung in formalin overnight for fixation. The following day, lungs were moved into 70% ethanol and stored at 4° C. until paraffin-embedding.

Cell Counts and Cell Differentials

Cell pellets were resuspended in 200 μl of PBS, then 10 μl of the solution was put onto a hemocytometer for total cell counts. For cell differentials, 150 μl of the suspended cell solution was put on a microscope slide using a cytospin. Using a Revolve light microscope (La Jolla, Calif.), a total of 300 cells were counted per slide, and were differentiated by cell type. The number of each cell type identified was then divided by 300 to get the percentage of each cell type amongst the total cell population, then that percentage was multiplied by the total cell count to represent the total number of each cell type in the BALF.

Mean Linear Intercept (MLI) Analysis

Mouse lungs were fixed in formalin and paraffin-embedded, then sectioned and stained in hematoxylin and eosin by the University of California Irvine Department of Pathology Experimental Tissue Resource Core Facility. The lungs were imaged on a Revolve light microscope (La Jolla, Calif.) at 10× magnification. MLI measurements were calculated using an established indirect method on ImageJ software. Briefly, alveolar walls/intersections were counted along a line of known length, then length was divided by the number of intersections to calculate MLI. This process was repeated for a total of five MLI measurements per image, with there being four images per mouse lung. The average MLI measurement for each lung was calculated and statistically analyzed using GraphPad Prism software (San Diego, Calif.).

Results

Figure 1A:
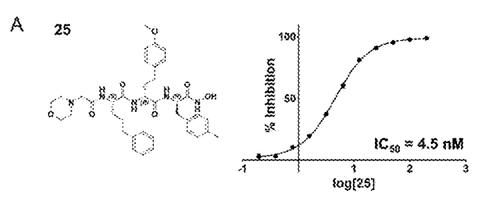
FIGS. 1A-1E. Chemical structures and comparative dose response values for optimized MMP-12 inhibitors. (A) Chemical structure of compound 25 and relative dose response curve for inhibitor of MMP-12. (B) Chemical structure of compound 26 and relative dose response curve for inhibitor of MMP-12. (C) Overlay of [$^{15}$N, $^1$H] sofast HMQC spectra of MMP-12 catalytic domain (10 μM) recorded in absence (blue) or in presence of compound 25 (red) or compound 26 (green), each at 10 μM. (D) Chemical structure of the pan-MMP inhibitor GM6001 and relative dose response curve for inhibition of MMP-12. (E) Chemical structure of compound MMP408 and relative dose response curve for inhibition of MMP-12.
Figure 1B:
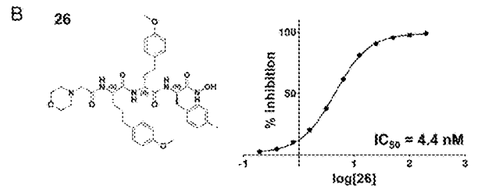
Figure 1C:
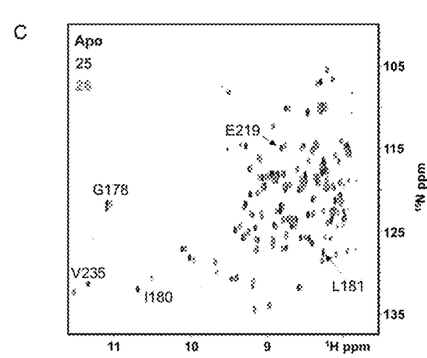
Figure 1D:
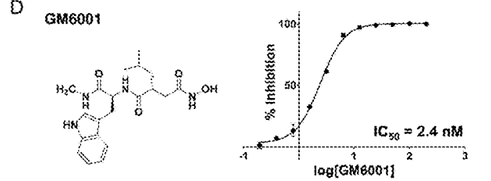
Figure 1E:
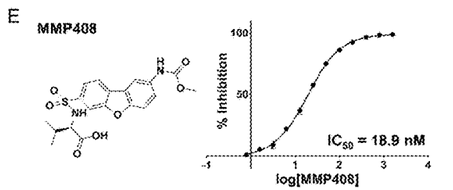

Enzyme activity inhibition assay using the SensoLyte® 520 MMP-12 Fluorimetric Assay Kit (Anaspec) revealed that compounds 25 and 26 were competitive inhibitors for MMP-12 with $IC_{50}$ values of ~ 4 nM (FIG. 1A, B). As controls, the pan-MMP inhibitor GM6001, and the reportedly potent and selective MMP-12 inhibitor compound MMP408 were also tested, When tested side by side, control agents pan-MMP inhibitor GM6001, and MMP-12 selective inhibitor MMP408 displayed $IC_{50}$ values of ~2.5 nM, and ~19 nM, respectively (FIG. 1D, E). While absolute $IC_{50}$ values depend on the assay parameters, the relative potency between compounds 25, 26, and MMP408, tested under the same experimental conditions, reveals that compounds 25 and 26 are >5 times more potent than MMP408.

Figure 2:
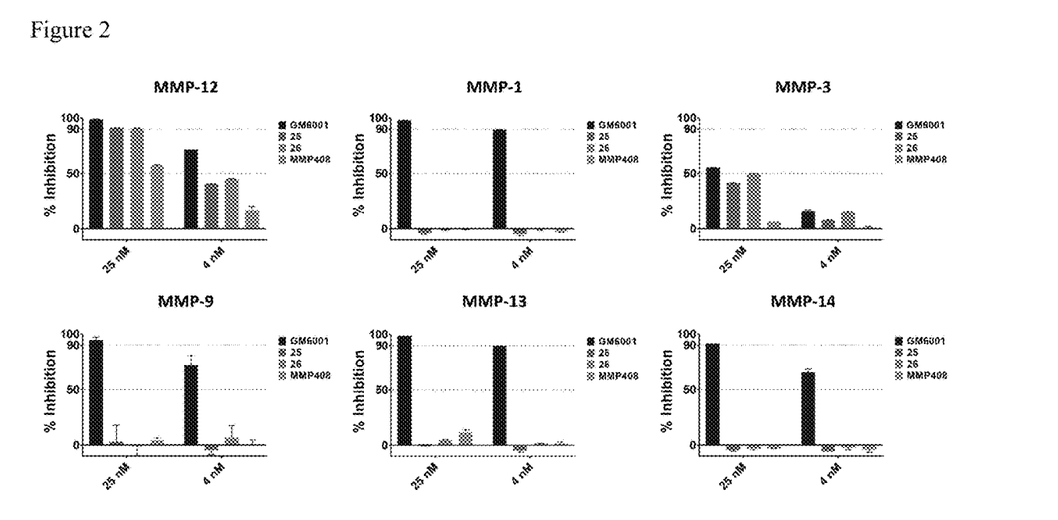
FIG. 2. Selectivity assays for compounds 25, 26, GM6001, and MMP408. For each indicated enzyme, agents were tested at 25 nM or at 4 nM and percent inhibition was measured using the catalytic domains of the respective enzyme and the SensoLyte® 520 Fluorimetric Assay Kit (Anaspec).

Compounds 25 and 26 did not display significant inhibition of MMP-1, MMP-9, MMP-13, and MMP-14, while appreciable inhibition of the closely related MMP-3 was observed with both agents and with GM6001 (FIG. 2).

Figure 3A:
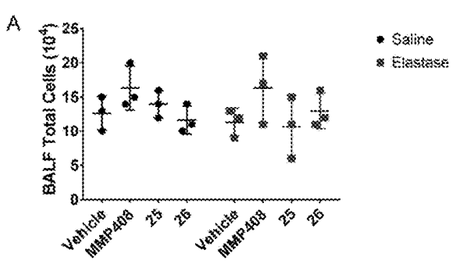
FIGS. 3A-3D. Effects of MMP-12 inhibition on lung lavage cellularity at 21 days post-PPE instillation. Mice were challenged with a single intranasal instillation of porcine pancreatic elastase, then treated daily for 7 days with vehicle control or MMP-12 inhibitors MMP408, compound 25, or compound 26 via intraperitoneal inoculation beginning 2 days following elastase treatment. Bronchoalveolar lavage was performed and fluid was assessed for total cells, and differential cell counts performed to enumerate individual cell populations. (A) Total BALF cells; (B) BALF macrophages; (C) BALF neutrophils; (D) BALF lymphocytes. ** $P<0.01$ versus Vehicle+Saline control, based on two-way ANOVA with Tukey post-hoc comparisons. Significant two-way ANOVA main effects indicated at top of graph.
Figure 3B:
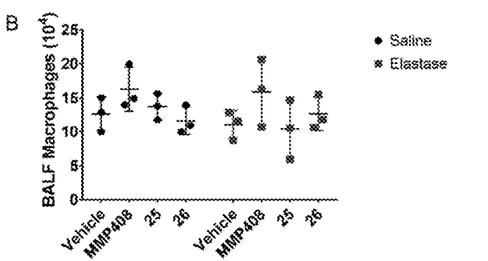
Figure 3C:
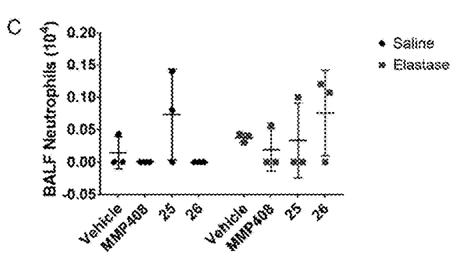
Figure 3D:
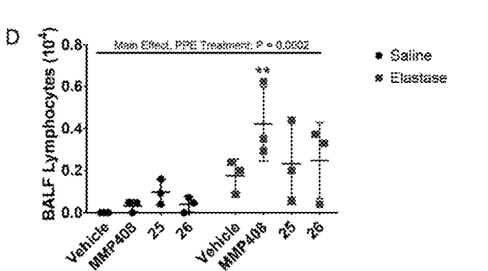

A preliminary pharmacokinetic study was also conducted with compound 25 (FIG. 3A). When administered at 30 mg/kg intraperitoneally, a peak plasma drug concentration reaching~400 ng/ml was observed corresponding to ~ 580 nM, hence>20 times above the in vitro determined $IC_{90}$ value.

Efficacy of Agents 25 and 26 in a Murine Model of Elastase-Induced Emphysema

Recent studies have identified a role for MMP-12 in promoting the emphysematous lung tissue destruction associated with chronic obstructive pulmonary disease. Compound 25 and compound 26 were evaluated in a murine model of elastase-induced emphysema. In this model, mice instilled with elastase exhibit early markers of inflammation and injury within hours to days following elastase treatment. While initial inflammatory cell influx and heightened airway cytokine release wane in the first week following elastase instillation, lung injury following elastase treatment evolves over several weeks, with dramatic tissue destruction evident within 3-4 weeks following elastase challenge. Using this model, the impacts of MMP-12 inhibition on the development of tissue destruction at 21 days following elastase treatment was assessed. There was not a significant difference in total BALF cellularity/influx amongst all groups (FIG. 3A), although differential cell analysis did identify a significant impact of elastase treatment on lymphocytes influx, as shown in FIG. 3.

Figure 4:
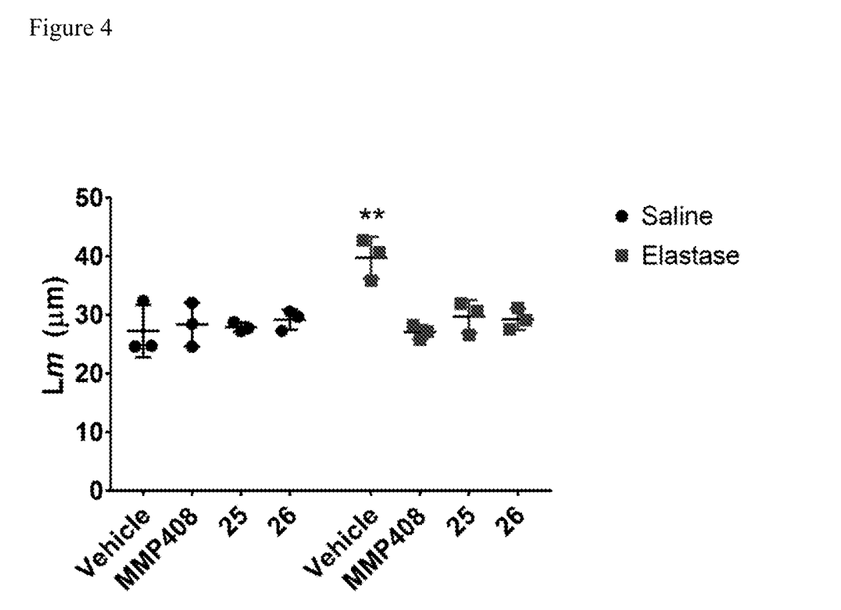
FIG. 4. Effects of MMP-12 inhibition on lung tissue destruction at 21 days post-PPE instillation. Mice were challenged with a single intranasal instillation of porcine pancreatic elastase, then treated daily for 7 days with vehicle control or MMP-12 inhibitors MMP408, compound 25, or compound 26 via intraperitoneal inoculation beginning 2 days following elastase treatment. At day 21, lungs were inflated in formalin at 20 cm pressure, and tissue were paraffin-embedded, sectioned, and stained with hematoxylin and eosin. Mean linear intercept analyses were performed to assess the impact of MMP-12 inhibition on PPE-induced lung tissue destruction as measured by increased mean linear intercept. ** $P<0.01$ versus Vehicle+Saline control, based on two-way ANOVA with Tukey post-hoc comparisons. Significant two-way ANOVA main effects indicated at top of graph.

To assess for tissue destruction in saline- or elastase-treated animals, a mean linear intercept (MLI) analysis was performed. Based on this analysis, significant lung tissue destruction in murine lungs exposed to porcine pancreatic elastase (PPE) and treated with the vehicle control, compared to murine lungs exposed to the saline control and treated with the vehicle control (FIG. 4) was seen. Notably, however, mice exposed to PPE but treated with MMP-12 inhibitors (MMP-408, compound 25, or compound 26) exhibited a significant decrease in emphysema-like pathology compared to PPE+vehicle-treated mice, with MLI measurements for mice treated with PPE+MMP-12 inhibitors exhibiting no significant differences compared to saline (no PPE)-treated mice (FIG. 4).

All publications, patents, and patent documents are incorporated by reference herein, as though individually incorporated by reference.

What is claimed is:

1. A compound selected from the group consisting of:

and or a salt thereof.

2. A pharmaceutical composition comprising a compound as described in claim 1 or a pharmaceutically acceptable salt thereof, and a pharmaceutically acceptable excipient.

\* \* \* \* \*